United States Patent [19]
Menig et al.

[11] Patent Number: 4,560,769  
[45] Date of Patent: Dec. 24, 1985

[54] PREPARATION OF PYRROLES

[75] Inventors: Helmuth Menig, Friedelsheim; Martin Fischer, Ludwigshafen; Karl Baer, Weinheim, all of Fed. Rep. of Germany

[73] Assignee: BASF Aktiengesellschaft, Ludwigshafen, Fed. Rep. of Germany

[21] Appl. No.: 588,119

[22] Filed: Mar. 9, 1984

[30] Foreign Application Priority Data

Mar. 16, 1983 [DE] Fed. Rep. of Germany ....... 3309355

[51] Int. Cl.$^4$ ................. C07D 207/323; C07D 295/00
[52] U.S. Cl. .................................... 548/560; 548/563; 548/564
[58] Field of Search ............... 548/578, 579, 563, 564, 548/560

[56] References Cited

U.S. PATENT DOCUMENTS 2,421,650  6/1947  Reppe et al. .................... 548/563 X
2,671,789  3/1954  Copes et al. ........................ 548/563

OTHER PUBLICATIONS

Ullmans Encycl. d. Techn. Chem., 19, (1980), pp. 639–642.
Murahashi et al.; J. C. S. Chem. Comm., (1974), pp. 931–932.

*Primary Examiner*—Joseph Paul Brust
*Attorney, Agent, or Firm*—John H. Shurtleff

[57] ABSTRACT

Pyrroles are prepared by a process in which ammonia or an amine is reacted with a but-2-ene-1,4-diol in the presence of a supported catalyst containing copper, silver, zinc, palladium, nickel, cobalt and/or platinum and/or compounds of these metals as catalytic materials, and in the presence or absence of compounds of chromium and/or manganese as additional catalysts, in the gas phase.

The pyrroles obtainable by the process of the invention are useful starting materials for the preparation of dyes, corrosion inhibitors, drugs and pesticides.

12 Claims, No Drawings

PREPARATION OF PYRROLES

The present invention relates to a process for the preparation of pyrroles by reacting ammonia or an amine with a but-2-ene-1,4-diol in the presence of a supported catalyst containing copper, silver, zinc, palladium, nickel, cobalt and/or platinum and/or compounds of these metals as catalytic materials, and in the presence or absence of compounds of chromium and/or manganese as additional catalysts, in the gas phase, at from 180° to 500° C.

Pyrroles are produced industrially by catalytic dehydrogenation of the corresponding pyrrolidines, for example over a Pd/Al$_2$O$_3$ catalyst. The pyrrolidines in turn are obtainable from, for example, butane-1,4-diol or tetrahydrofuran and ammonia or alkylamines (Ullmans Encycl. d. techn. Chem. (1980), Volume 19, pages 639-642). With regard to simplicity and economy of operation, this process has the disadvantage that a two-step procedure starting from a 1,4-diol or tetrahydrofuran is required, and the corresponding pyrrolidine has to be isolated, for example by distillation.

A single-stage synthesis of N-alkylpyrroles is described in J. Chem. Soc. Chem. Comm., 1974, 931-932. But-2-ene-1,4-diol is reacted with cyclohexylamine or another relatively high-boiling amine in the liquid phase, in the presence of palladium black, for from 14 to 20 hours at 120° C.:

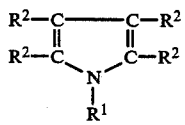

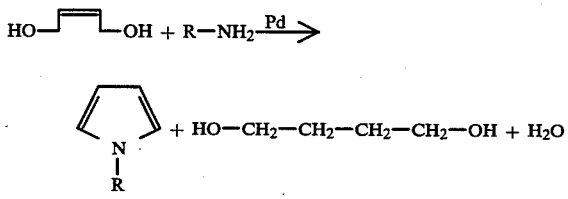

However, the process has the disadvantages that palladium black is employed in an amount of about 3% by weight, based on but-2-ene-1,4-diol, and is therefore an expensive catalyst, 1 mole of 2-butene-1,4-diol is obtained per mole of pyrrole formed, and the reaction velocity is very low (space-time yield: Less than 15 g of pyrrole per liter of reaction volume per hour).

We have found that pyrroles of the formula

where the individual radicals R$^1$ and R$^2$ can be identical or different and are each hydrogen or an aliphatic, cycloaliphatic, araliphatic or aromatic radical, are advantageously obtained by reacting a nitrogen compound with a but-2-ene-1,4-diol in the presence of a catalyst if ammonia or an amine of the formula $$R^1-NH_2 \qquad II$$

where R$^1$ has the above meanings, is reacted with a but-2-ene-1,4-diol of the formula

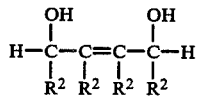

where R$^2$ has the above meanings, in the presence of
 (a) copper, silver, zinc, palladium, nickel, cobalt and/or platinum and/or
 (b) compounds of these metals as catalysts and in the presence or absence of
 (c) compounds of chromium and/or manganese as additional catalysts
 (d) on a carrier,
in the gas phase, at from 180° to 500° C.

Where methylamine and but-2-ene-1,4-diol are used, the reaction can be represented by the following equation:

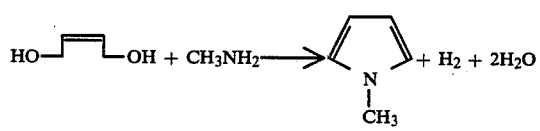

Compared with the prior art, the process according to the invention gives pyrroles in good yield and purity and in better space-time yield, by a simpler and more economical route. In general, space-time yields of from 54 to 165 g of pyrrole per liter of supported catalyst per hour are obtained in accordance with the invention. The catalysts, or the amounts of catalysts used, are more economical compared with the conventional processes. The process according to the invention is particularly suitable for large-scale industrial use and continuous operation. In view of the prior art, all these advantages of the novel process are surprising. Particularly in comparison with the process described in J. Chem. Soc. (loc. cit.), it was to be expected that, at the higher temperatures according to the invention, poorer yields would be obtained and that moreover half the starting material would be converted to butane-1,4-diols.

The starting materials II are reacted with the starting materials III in stoichiometric amounts or in excess, preferably in an amount of from 0.1 to 10, in particular from 1 to 4, moles of starting material II per mole of starting material III. Preferred starting materials II and III, and accordingly preferred end products I, are those of the formulae in which the individual radicals R$^1$ and R$^2$ can be identical or different and are each hydrogen, alkyl of 1 to 8 carbon atoms, cycloalkyl of 5 to 8 carbon atoms, alkylaryl or aralkyl of 7 to 12 carbon atoms, or phenyl. The abovementioned radicals can be further substituted by groups which are inert under the reaction conditions, e.g. alkyl groups of 1 to 4 carbon atoms.

In addition to ammonia, amines which can be used for the preparation of the corresponding pyrroles I are primary amines which can be vaporized without decomposition, e.g. methylamine, ethylamine, n-propylamine, i-propylamine, n-butylamine, i-butylamine, s-butylamine, n-pentylamine, 3-methyl-1-butylamine, 3-methyl-2-butylamine, 2-methyl-2-butylamine, n-hexylamine, n-octylamine, 2-ethyl-1-hexylamine, cyclohexylamine, benzylamine, aniline, 2-phenylethylamine and toluidine.

Examples of suitable starting materials III for the reaction according to the invention are but-2-ene-1,4- diol, 2-methylbut-2-ene-1,4-diol, 2,3-dimethylbut-2-ene-1,4-diol, pent-2-ene-1,4-diol, 2-methylpent-2-ene-1,4-diol, hex-2-ene-1,4-diol, hex-3-ene-2,5-diol, hept-2-ene-1,4-diol, hept-3-ene-2,5-diol, oct-2-ene-1,4-diol, oct-3-ene-2,5-diol, oct-4-ene-3,6-diol, 1-phenylbut-2-ene-1,4-diol, 1-phenylpent-2-ene-1,4-diol, 1-phenylpent-3-ene-2,5-diol, 1-phenylhex-3-ene-2,5-diol, 1-cyclohexylbut-2-ene-1,4-diol and 1-(p-tolyl)-but-2-ene-1,4 -diol.

Examples of end products I which can be prepared from the starting materials II and III are pyrrole, 1-methylpyrrole, 1-ethylpyrrole, 1-n-propylpyrrole, 1-i-propylpyrrole, 1-n-butylpyrrole, 1-i-butylpyrrole, 1-s-butylpyrrole, 1-n-pentylpyrrole, 1-(3-methylbut-1-yl)-pyrrole, 1-(3-methybut-2-yl)-pyrrole, 1-(2-methylbut-2-yl)-pyrrole, 1-n-hexylpyrrole, 1-n-octylpyrrole, 1-(2-ethylhex-1-yl)-pyrrole, 1-cyclohexylpyrrole, 1-benzyl-pyrrole, 1-phenylpyrrole, 1-(2-phenylethyl)-pyrrole, 3-methylpyrrole, 3,4-dimethylpyrrole, 2-methylpyrrole, 2,4-dimethylpyrrole, 2,5-dimethylpyrrole, 1,2-dimethylpyrrole, 1,3-dimethylpyrrole, 1,2,4-trimethylpyrrole, 1,3,4-trimethylpyrrole, 1,2,5-trimethylpyrrole, 2-ethylpyrrole, 1-methyl-2-ethylpyrrole, 2-phenylpyrrole, 1-methyl-2-phenylpyrrole, 2-benzylpyrrole, 1-methyl-2-benzylpyrrole, 2-cyclohexylpyrrole and 2-(p-tolyl)-pyrrole.

The reaction is carried out at from 180° to 500° C., preferably from 240° to 350° C., under atmospheric or superatmospheric pressure, continuously or batchwise. The reaction temperature should be sufficiently high to keep the reaction mixture in the gaseous state. In the case of relatively high-boiling diols, this can also be achieved with the aid of an inert gas. The residence times are advantageously from 1 to 40, preferably from 5 to 25, seconds. It is advantageous if no additional solvent is used. If required, the amine II, e.g. methylamine, can be fed to the reaction in the form of its solution in a suitable solvent which is inert under the reaction conditions, e.g. water. In such cases, the solvent is advantageously used in an amount of from 100 to 10,000, preferably from 100 to 300, % by weight, based on starting material II.

The reaction mixtures are generally vaporized and fed to the reaction mixture in the vapor state, either separately from one another or, advantageously, as a mixture. If required, gases which are inert under the reaction conditions can be used as diluents for the gas mixture. Furthermore, to promote vaporization, such inert gases can be passed through one or both starting materials during vaporization. Gases which are inert under the reaction conditions (inert gases) and which are advantageously used are alkanes, such as methane, ethane, propane, 2,2-dimethylpropane, butane, pentane or isobutane, but preferably nitrogen, steam and/or carbon dioxide, as well as mixtures of these. Advantageously, not less than 0.1, preferably from 0.2 to 100, in particular from 0.2 to 10, g of inert gas per g of starting material II or III are used. The flow velocity of the inert gas passed through the reaction mixture is preferably from 0.1 to 100, particularly preferably from 0.1 to 5, moles per hour per mole of starting material II.

Suitable catalysts are silver, zinc, palladium, nickel, cobalt, platinum and/or copper, as metals and/or compounds thereof, individually or as a mixture with one another, in the form of supported catalysts. The catalyst can contain one or more metals, or one or more metal compounds, or one metal and one or more metal compounds together, or several metals and one or more metal compounds. The copper compounds can be those of monovalent or divalent copper; accordingly, the other metals can also be present in their compounds in various valence states. Advantageous compounds are the acetates, formates, hydroxides, nitrates, phosphates, sulfates, oxalates, carbonates and, preferably, oxides of the above metals. Advantageously the catalyst contains silver, palladium, platinum, copper, nickel and cobalt as metals, and zinc in the form of a metal compound. Advantageous catalysts are those containing from 1 to 3 components (metals and/or metal compounds). In a preferred embodiment, metal compounds are combined with the carrier, and the compound or compounds are then reduced to the metal or metals. In this context, a supported catalyst is a catalyst (individual metal or individual compound or several components) on a carrier (consisting of one or more materials). In general, the catalyst (not including the carrier) is used in an amount corresponding to 0.01–10, preferably 0.05–1, % by weight, based on starting material II, of total metal; total metal is defined as the overall sum of free metal and of metal or metals bonded in any form e.g. salt form, addition compound, complex or alloy, in the catalyst. In continuous operation, it is advantageous to use a throughput of from 0.1 to 100, preferably from 1 to 50, g of starting material III per g of catalyst (not including the carrier) per hour.

If required, it is also possible to use compounds, advantageously oxides, of chromium and/or manganese as additional catalysts, advantageously in an amount corresponding to 1–500, in particular 10–200, % by weight, based on the weight of catalytic metal in the principal catalyst, of additional metals. Where additional catalysts are used, the abovementioned parameter ranges and statements regarding catalytic materials for the principal catalyst apply; total metal is then the total metal of the principal catalyst. As in the case of the principal catalyst, the additional metal is understood as meaning the overall sum of the additional metal components, regardless of the form in which the one or more metal compounds are present in the additional catalyst.

The catalyst, with or without the additional catalytic compound, is expediently applied onto a carrier, advantageously in an amount of from 0.2 to 25% by weight, based on the weight of the carrier. Suitable carriers are silica compounds, such as silicates, e.g. sodium aluminum silicate, calcium aluminum silicate, bleaching earths, fuller's earth, clays, kaolin, allophanes, zeolites, montmorillonite, pumice, Florida earth, quartz, asbestos, mullite or bentonite; precipitated silica, silica gel or kieselguhr; titanium dioxide, zirconium dioxide, tin dioxide, magnesium oxide, magnesite or active carbon; alkaline earth metal sulfates or alkaline earth metal phosphates, e.g. the calcium or barium salts; metal oxides which, when calcined with a boron compound, form the corresponding metal borates, e.g. calcium oxide; and appropriate mixtures of the stated carriers. It may be advantageous to add sodium carbonate and/or potassium carbonate, expediently in the form of their 0.5–20% strength by weight aqueous solutions, to the carrier; amounts of from 0.5 to 10% by weight, based on the weight of the carrier, of metal carbonate are advantageous. The supported catalysts are prepared by a conventional method, for example by applying the metal compound and, if required, the additional metal compound onto the carrier, drying and calcining, for example at between 400° and 1,200° C., in a reducing, oxidizing or inert atmosphere. The carrier, in its desired geometrical form, can also be impregnated with a solution of the metal compound and, if required, of the additional metal compound, and then dried. It is also possible to knead the carrier with the metal compound, and if required the additional metal compound, and water, to bring the mixture to the desired form, to dry this and to calcine it at from 400° to 1,200° C.

Examples of advantageous methods of preparing the catalyst are:

(1) The catalyst metal together with an additive (sodium carbonate or potassium carbonate) is applied onto $SiO_2$ powder or extrudates by impregnation with solutions of the metal nitrates and additional carbonates, followed by evaporation to dryness. Thereafter, the supported catalyst is heated at 500° C. for from 1 to 8 hours, and reduced in a stream of hydrogen at 200° C.

(2) An additional compound (sodium carbonate or potassium carbonate) is first applied onto $SiO_2$ extrudates or powder by impregnation with aqueous solutions of these compounds, and the product is then dried at 150° C. The carrier pretreated in this manner is then impregnated with an aqueous solution of the metal nitrate, and reduction is effected by heating for from 2 to 24 hours at 200° C. in a stream of hydrogen. If palladium(II) chloride solution is used for the impregnation, reduction is advantageously carried out using alkaline formalin solution or 5% strength by weight hydrazine solution.

(3) Silica and a basic oxide (e.g. MgO) are mixed thoroughly in a kneader. This mixture is heated at 450° C. for 6 hours, after which it is impregnated with a solution of the metal nitrates and then reduced for from 2 to 12 hours at 300° C. in a stream of hydrogen.

The particle sizes of the supported catalysts are preferably from 0.05 to 7 mm. Any desired shape can be chosen, for example pill-shaped, cylindrical, in the form of extrudates, spherical or gritty.

The supported catalysts are expediently employed in the form of chips, grit or spheres in a fluidized bed, the catalyst particles used advantageously having a size of from 0.005 to 3.0, in particular from 0.1 to 1.0, mm. The height of the catalyst bed is advantageously chosen so that the residence times of the starting materials II in the catalyst layer are from 1 to 100, preferably from 5 to 25, seconds. Regarding the preparation of the catalysts, reference may be made to Houben-Weyl, Methoden der organischen Chemie, Volume 4/2, page 142 et seq., and to Ullmanns Encyclopädie der technischen Chemie, Volume 9, page 271 et seq.

The reaction can be carried out as follows: the gaseous starting materials II and III, if appropriate mixed with inert gases, are passed over the supported catalyst in a fixed bed, at the reaction temperature. The reaction mixture which leaves the reactor in vapor form is, if required, then freed from dust in a cyclone and is condensed in a cooled vessel, where as a rule 2 phases form, and the end product is isolated by fractional distillation of the phases. Unreacted starting material can be recycled to the reaction.

In an advantageous embodiment of the process, the starting material is converted in a fluidized bed, at the reaction temperature. The supported catalyst is advantageously maintained as a fluidized bed using an inert gas, a mixture of starting material III and/or starting material II in vapor form with an inert gas or the starting materials alone as a fluidizing gas, preferably under reduced pressure. Accordingly, the total amount or a part of the starting materials can be passed into the fluidized-bed reactor separately from the fluidizing gas.

The process according to the invention can be carried out in a simple or subdivided, open or closed fluidized-bed system, with or without circulation of the fluidized catalyst. Regarding reactors, procedure, versions and reaction conditions for the fluidized-bed process, reference may be made to Ullmanns Encyclopädie der technischen Chemie, Volume 1, page 916 et seq. The reaction mixture is worked up in the manner stated above.

The pyrroles which can be prepared by the process of the invention are useful starting materials for the preparation of dyes, corrosion inhibitors, drugs and pesticides. Regarding the use of these compounds, reference may be made to the abovementioned publications, U.S. Pat. No. 3,008,965, Ullmanns Encycl. d. techn. Chem. (1963), Volume 14, pages 505–510, and French Pat. No. 1,574,570.

In the Examples which follow, percentages by weight are based on the weight of the supported catalyst (=catalyst and carrier).

EXAMPLE 1

The reaction was carried out in an electrically heated vertical tubular reactor having an internal diameter of 28 mm and a height of 450 mm. A supported catalyst (198 g, 350 ml) containing 8% by weight of metallic copper on pumice (pumice stones having a diameter of 3–5 mm) was introduced into the reaction tube and heated to 250° C. A gas mixture consisting of but-2-ene-1,4-diol and monomethylamine, fed in by a cocurrent procedure, was passed continuously over this catalyst.

The feed rates were 0.6 mole/hour of diol III and 0.66 mole/hour of amine II. After leaving the reactor, the product was cooled to 22° C., and 2 phases formed. According to gas chromatographic analysis, the organic phase contained 59% by weight of 1-methylpyrrole, while the aqueous phase contained 3% by weight of 1-methylpyrrole; this corresponds to a total yield of 57%. The end product was isolated by distillation. The results are shown in Table 1.

EXAMPLE 2

The procedure described in Example 1 was followed, except that the catalyst used (248 g, 410 ml) was in the form of extrudates (4 mm diameter, 10 mm length) and contained 0.5% by weight of metallic palladium and 5% by weight of metallic copper on $SiO_2$. The results are shown in Table 1.

EXAMPLE 3

The procedure described in Example 1 was followed, except that the catalyst used (192 g, 325 ml) contained 0.5% by weight of metallic palladium and 5% by weight of metallic silver on $SiO_2$. The results obtained are summarized in Table 1.

EXAMPLE 4

The procedure described in Example 1 was followed, except that the catalyst used (223 g, 350 ml) contained 0.5% by weight of metallic palladium, 5% by weight of metallic silver and 5% by weight of magnesium oxide on $SiO_2$. The results obtained are summarized in Table 1.

EXAMPLE 5

The procedure described in Example 1 was followed, except that the catalyst used (207 g, 350 ml) contained 0.5% by weight of metallic palladium, 5% by weight of metallic silver and 2% by weight of potassium oxide on SiO$_2$. The results obtained are summarized in Table 1.

EXAMPLE 6

The procedure described in Example 1 was followed, except that the catalyst used (220 g, 350 ml) contained 0.5% by weight of metallic palladium, 5% by weight of metallic silver and 1.35% by weight of Mn$_3$O$_4$ on SiO$_2$. The results obtained are summarized in Table 1.

EXAMPLE 7

The procedure described in Example 1 was followed, except that the catalyst used (195 g, 350 ml) contained 5% by weight of metallic silver on SiO$_2$. The results obtained are summarized in Table 1.

EXAMPLE 8

The procedure described in Example 1 was followed, except that the catalyst used (181 g, 410 ml) contained 0.7% by weight of metallic palladium on SiO$_2$. The results obtained are summarized in Table 1.

EXAMPLE 9

The procedure described in Example 1 was followed, except that the catalyst used (825 g, 170 ml) contained 0.7% by weight of metallic palladium and 2% by weight of sodium oxide on SiO$_2$. But-2-ene-1,4-diol was fed in at a rate of 0.45 mole/hour, while aqueous methylamine solution (40% by weight) was fed in at a rate corresponding to 0.68 mole/hour of methylamine. The results are summarized in Table 1.

EXAMPLE 10

The procedure described in Example 1 was followed, except that the catalyst used (358 g, 405 ml) contained 25.6% by weight of metallic cobalt on SiO$_2$. The results obtained are summarized in Table 1.

EXAMPLE 11

The procedure described in Example 7 was followed, except that the feed rates were increased to 0.9 mole/hour of the diol III and 0.99 mole/hour of the amine II. The organic phase of the reacted mixture contained 90.1% by weight of 1-methylpyrrole, while the aqeuous phase contained 3.0% by weight of 1-methylpyrrole; this corresponds to a total yield of 62%.

EXAMPLE 12

The procedure described in Example 7 was followed, except that the feed rate was doubled. The results obtained are summarized in Table 1.

TABLE 1

| Example No. | Conversion [%] | Yield (% of theory) | Space-time yield (g of pyrrole per liter of catalyst per hour) |
| --- | --- | --- | --- |
| 1 | 99 | 57 | 78 |
| 2 | about 100 | 47 | 56 |
| 3 | 96 | 60 | 91 |
| 4 | 99 | 59 | 82 |
| 5 | 95 | 57 | 80 |
| 6 | 94 | 43 | 65 |
| 7 | 95 | 70 | 98 |
| 8 | 95 | 46 | 54 |
| 9 | 90 | 40 | 87 |
| 10 | 85 | 45 | 55 |
| 11 | 79 | 62 | 129 |
| 12 | 77 | 59 | 165 |

The end product of Examples 1–13, i.e. 1-methyl-pyrrole, had a boiling point of 110°–113° C.

EXAMPLE 13

The procedure described in Example 1 was followed, using 192 g of the catalyst described in Example 3. A gas mixture consisting of 2-methylbut-2-ene-1,4-diol (0.51 mole/hour) and methylamine (0.56 mole/hour) was passed over this catalyst. The results obtained are summarized in Table 2.

EXAMPLE 14

The procedure described in Example 1 was followed, using 192 g of the catalyst described in Example 3. A gas mixture consisting of but-2-ene-1,4-diol (0.6 mole/hour) and n-butylamine (0.6 mole/hour) was passed over this catalyst. The results obtained are summarized in Table 2.

EXAMPLE 15

The procedure described in Example 1 was followed, using 192 g of the catalyst described in Example 3. A gas mixture consisting of but-2-ene-1,4-diol (0.6 mole/hour) and cyclohexylamine (0.6 mole/hour) was passed over this catalyst. The results obtained are summarized in Table 2.

EXAMPLE 16

The procedure described in Example 1 was followed, using 192 g of the catalyst described in Example 3. A gas mixture consisting of but-2-ene-1,4-diol (0.61 mole/hour) and ammonia (0.66 mole/hour) was passed over this catalyst. The results obtained are summarized in Table 2.

TABLE 2

| Example No. | Diol | Amine | End product | Bp. in °C. (mbar) | Conversion (%) | Yield (% of theory) |
| --- | --- | --- | --- | --- | --- | --- |
| 13 | 2-methylbut-2-ene-1,4-diol | CH$_3$NH$_2$ | 2-methyl-1-methylpyrrole | 62 (87) | 85 | 59 |
| 14 | but-2-ene-1,4-diol | C$_4$H$_9$NH$_2$ | 1-n-butylpyrrole | 54 (10) | 86 | 53 |

TABLE 2-continued

| Example No. | Diol | Amine | End product | Bp. in °C. (mbar) | Conversion (%) | Yield (% of theory) |
|---|---|---|---|---|---|---|
| 15 | | cyclohexyl-NH₂ | N-cyclohexyl pyrrole | 96–100 (11–13) | 88 | 41 |
| 16 | | NH₃ | pyrrole (NH) | 135 | 50 | 35 |

We claim:

1. A process for the preparation of a pyrrole of the formula $$\begin{array}{c} R^2-C\!\!=\!\!=\!\!C-R^2 \\ \| \quad\quad \| \\ R^2-C \quad\quad C-R^2 \\ \diagdown N \diagup \\ | \\ R^1 \end{array} \quad\quad I$$

where the individual radicals $R^1$ and $R^2$ can be identical or different and are each hydrogen or alkyl with 1 to 8 carbon atoms, cycloalkyl with 5 to 8 carbon atoms, alkylaryl or aralkyl with 7 to 12 carbon atoms or phenyl, which process comprises:

reacting 0.1 to 10 moles of ammonia or an amine of the formula $$R^1\!-\!NH_2 \quad\quad II$$

where $R^1$ has the above meanings, with 1 mole of a but-2-ene-1,4-diol of the formula $$\begin{array}{c} OH \quad\quad OH \\ | \quad\quad | \\ H-C-C\!=\!C-C-H \\ | \;\; | \;\; | \;\; | \\ R^2 \, R^2 \, R^2 \, R^2 \end{array} \quad\quad III$$

where $R^2$ has the above meanings, in the gas phase, at a temperature from 180° to 500° C., and in the presence of a metal catalyst selected from the group consisting of silver and a mixture of silver and palladium, said catalyst being applied to a carrier, and said catalyst being used in an amount, calculated as total metal without carrier, corresponding to 0.01–10% by weight, based on starting material II, of total metal; and
using a throughput of from 0.1 to 100 g of starting material III per g of catalyst calculated without carrier per hour.

2. A process as claimed in claim 1, wherein the reaction is carried at from 240° to 350° C.

3. A process as claimed in claim 1, wherein the reaction is carried out during a residence time of from 1 to forty seconds.

4. A process as claimed in claim 1, wherein the reaction is carried out in the presence of not less than 0.1 g of inert gas per g of starting material II or III.

5. A process as claimed in claim 4, wherein the reaction is carried out with the inert gas being passed through the reaction mixture at a flow velocity of from 0.1 to 100 moles per hour per mole of starting material II.

6. A process as claimed in claim 1, wherein the reaction is carried out using the catalyst on a carrier in an amount of from 0.2 to 25% by weight, based on the weight of the carrier.

7. A process as claimed in claim 1, wherein the reaction is carried out using an oxide of a metal selected from the group consisting of chromium or manganese or a mixture thereof as an additional catalyst in an amount of from 1 to 500% by weight of total additional metal, based on the weight of catalytic metal in the principal catalyst.

8. A process as claimed in claim 1 wherein the catalyst is applied to $SiO_2$ as the carrier.

9. A process as claimed in claim 1 wherein the catalyst is a mixture of silver and palladium applied to $SiO_2$ as the carrier.

10. A process as claimed in claim 1 wherein the catalyst is a mixture of the metals silver and palladium applied to $SiO_2$ mixed with magnesium oxide as the carrier.

11. A process as claimed in claim 1 wherein the catalyst is a mixture of the metals silver and palladium applied to $SiO_2$ mixed with potassium oxide as the carrier.

12. A process as claimed in claim 7 wherein the catalyst is a mixture of silver and palladium together with manganese oxide applied to $SiO_2$ as the carrier.

* * * * *